United States Patent [19]

Ford et al.

[11] 4,438,329

[45] Mar. 20, 1984

[54] MINIMIZING THE EFFECT OF SPURIOUS PHOTODETECTOR CURRENTS IN FLASH SPECTROFLUORIMETRY

[75] Inventors: Michael A. Ford, Maidenhead; Brian B. Leather, Beaconsfield, both of England

[73] Assignee: Perkin-Elmer Limited, Buckinghamshire, England

[21] Appl. No.: 373,072

[22] Filed: Apr. 29, 1982

[30] Foreign Application Priority Data

May 5, 1981 [GB] United Kingdom ............... 8113636

[51] Int. Cl.³ .................................................. G01N 21/64
[52] U.S. Cl. .................................. 250/459.1; 250/461.1
[58] Field of Search ............... 250/365, 458.1, 459.1, 250/461.1, 461.2; 364/413

[56] References Cited

U.S. PATENT DOCUMENTS 3,787,695 1/1974 West ...................................... 250/365
4,049,970 9/1977 Ford .................................. 250/461.2

FOREIGN PATENT DOCUMENTS 2013334 8/1979 United Kingdom .

Primary Examiner—Davis L. Willis
Attorney, Agent, or Firm—F. L. Masselle; E. T. Grimes; R. A. Hays

[57] ABSTRACT

The vitiating effect on the fluorescence measuring signal of extraneous currents flowing through the fluorescence detection means in flash spectrofluorimetry is almost completely eliminated by integrating the output of the fluorescence measuring means for the duration of the signal period, which includes a flash duration, and again for an equal period occurring between flashes which therefore does not include a flash duration. The second integral is then subtracted from the first to obtain a fluorescence measuring signal substantially unaffected by extraneous currents, such as dark current, sample phosphorescence, etc. The invention is applicable to single- and double-channel operation. In the latter, in addition to the fluorescence measuring channel there is provided a fluorescence reference channel. This enables the fluorescence measuring signal and the fluorescence reference signal to be ratioed together, the effect of extraneous currents having first been eliminated in both.

15 Claims, 2 Drawing Figures

MINIMIZING THE EFFECT OF SPURIOUS PHOTODETECTOR CURRENTS IN FLASH SPECTROFLUORIMETRY

BACKGROUND OF THE INVENTION

This invention generally relates to flash spectrofluorimetry, in which a sample under analysis is subjected to flashes of exciting radiation of very short duration compared with a dwell time allowed between flashes and the fluorescence emitted by the sample is measured by a photodetector in order to derive a fluorescence measuring signal characteristic of the sample; in particular, the invention relates to method of and apparatus for flash spectrofluorimetry wherein the fluorescence measuring signal is substantially freed from the vitiating effect thereon of any spurious currents, e.g. dark current, flowing through the photodetector, in particular currents occurring simultaneously with the said signal. Although spurious currents may arise in different ways—as will be later indicated—their net effect is the setting up in the photodetector of a "standing current" that masks the true value of the fluorescence measuring signal, whether said signal is evaluated as a current or a voltage output.

A spark source, or alternatively a continuously energized source cooperating with a light chopper, may of course be used in flash spectrofluorimetry, but in the present state of the art the best balance of operational and constructional advantages resulting from intermittent irradiation is achieved by the use of a plasma discharge source supplied with energization pulses which are (a) of very short duration (measured in microseconds) and sufficiently high peak power (measured in kilowatts) to raise the plasma produced on discharge to the colour temperature required for a continuum of light to be emitted, and (b) of sufficiently low repetition rate (dwell between pulses measured in milliseconds) to ensure that the average power dissipated by the source is maintained within reasonable bounds (typically within tens of watts) so that the life of the source is not unduly curtailed. One notable operational advantage resulting is the ease with which weakly fluorescing samples may be subjected to high level of excitation without any risk of damaging them. Constructionally, the comparatively small power supply required is a significant bonus, but more important, of course, is the closer approximation to the ideal source geometry that can be realized by the compactness of design permitted by the low average power dissipation.

It will be stressed later that the plasma discharge source is the preferred source in the context of the present invention since, in addition to the advantages referred to, it actually facilitates the realization of the present invention by enabling the fluorescence measuring signal to be evaluated over a very short interval of a few tens of microseconds.

An early example of flash spectrofluorimetry in which pulsed high-intensity irradiation of a sample is provided by a plasma discharge source is described in U.S. Pat. No. 3,787,695. In that example the fluorescence of the sample substantially coincident with the duration of each flash is analyzed by scanning it with a continuous interference filter, at a slow enough rate of displacement relative to the flashing frequency to include a conveniently large number of flashes in one complete scan travel, the scan output being detected with a photomultiplier and finally integrated for presentation on a chart recorder. To attenuate the effect of light source fluctuation on the recorded output, a reference photomultiplier is used in addition to the sample photomultiplier and their respective outputs are ratioed. This scheme works well but cannot combat the spurious responses introduced by unavoidable out-of-balances between the two outputs in terms of dark current characteristics, stray light, etc.

In the prior art specification referred to, the flash duration is contained within a few microseconds and the dwell between flashes is some 20 milliseconds. This means that the signal content of each photomultiplier output is of a very short duration compared with the spurious content due to the standing current flowing between successive flashes. In other words, the dark current contribution arising during the dwell period is a major cause of the out-of-balances.

In U.S. Pat. No. 4,049,970, assigned to the present applicant, the problem caused by the out-of-balances was greatly minimized by gating the photomultipliers so that they were only active for the signal duration (i.e. for the duration of the actual fluorescence measuring signal), the effect of any standing current flowing simultaneously with the signal being regarded as too small to be troublesome. The art has now progressed to the point where the effect can no longer be regarded as insignificant in terms of the fidelity of the fluorescence signal measurement, bearing in mind that dark current is not the only spurious factor to be accounted for, other significant factors such as stray light, sample phosphorescence (in measuring fluorescence any contribution to the photodetector output due to phosphorescence of the sample is spurious, of course) and so forth being also present.

SUMMARY OF THE INVENTION

The object of the present invention is to provide method of and apparatus for flash spectrofluorimetry in which the vitiating effect on the fluorescence measuring signal of any spurious contributions thereto due to the standing current flowing through the fluorescence measuring means both during the fluorescence signal period (including both signal rise and decay) and the dwell period between excitation flashes is substantially eliminated.

In broad terms the above object is achieved by integrating substantially the whole of the combined signal representing the resultant of the true fluorescence measuring signal and the spurious contribution thereto during a brief first time interval including the flash duration, sampling and integrating during a second, substantially equal, time interval occurring within the dwell period what the spurious contribution alone is in that second interval and subtracting the integrated sampled value from the integrated value of the combined signal to obtain the integral of the fluorescence measuring signal substantially free from the vitiating contribution due to the standing current.

In accordance with one aspect of the invention, the integrals are obtained in the analogue mode and the same instrumental means are used to evaluate them on a time-sharing basis. This has the advantage of avoiding the vitiating effect of the instrumental differences that would be met if separate integrators were used.

In accordance with another aspect of the invention, both integrals are converted from analogue to digital form before the subtraction hereinbefore referred to is carried out digitally. Again, common analogue-to-digital conversion means may be used to achieve the aforesaid advantage.

In accordance with a still further aspect of the invention, the method and the apparatus may be adapted for double-channel flash spectrofluorimetry, the provisions included in the sample measuring channel being largely repeated in a reference measuring channel and the "clean" (i.e. substantially free from spurious contribution) sample fluorescence measuring signal being ratioed with the "clean" reference fluorescence measuring signal in order to combine the well known advantages of ratio measuring with those accruing from the present invention.

When double-channel operation is adopted, the analogue-to-digital conversion means may be time-shared between channels. This will further enhance the high measuring performance made possible by the present invention, in that it will further reduce the effect of instrumental variations on the final fluorescence measuring signal.

The preferred source of exciting radiation for exciting the fluorescent sample in carrying the present invention into effect is the plasma discharge source, which permits the integration time of the combined signal (and hence the integration time of the spurious contribution sampled in the dwell period) to be made quite short (a few tens of microseconds will suffice), thus keeping the spurious signal content low and less changeable in both integrals without any sacrifice of sensitivity. Provided the second integration time follows the first pretty closely (i.e. within a small fraction of the dwell period), substantial cancellation of the spurious contribution to the fluorescence measuring signal is readily achieved.

BRIEF DESCRIPTION OF THE DRAWINGS

In FIG. 1, a source of flashed radiation, respresented by a pulsed Xenon-filled plasma discharge lamp 1, is arranged to irradiate a sample 2, the radiation first passing through an excitation monochromator 3 and a beam splitter 4. The fluorescence emitted by sample 2 traverses a fluorescence emission monochromator 5 and finally impinges upon a sample detector in the form of a sample photomultiplier 6, having an anode 6A and a cathode 6B. Photomultiplier 6 is, of course, screened from the direct rays issuing from the lamp 1.

Figure 1:
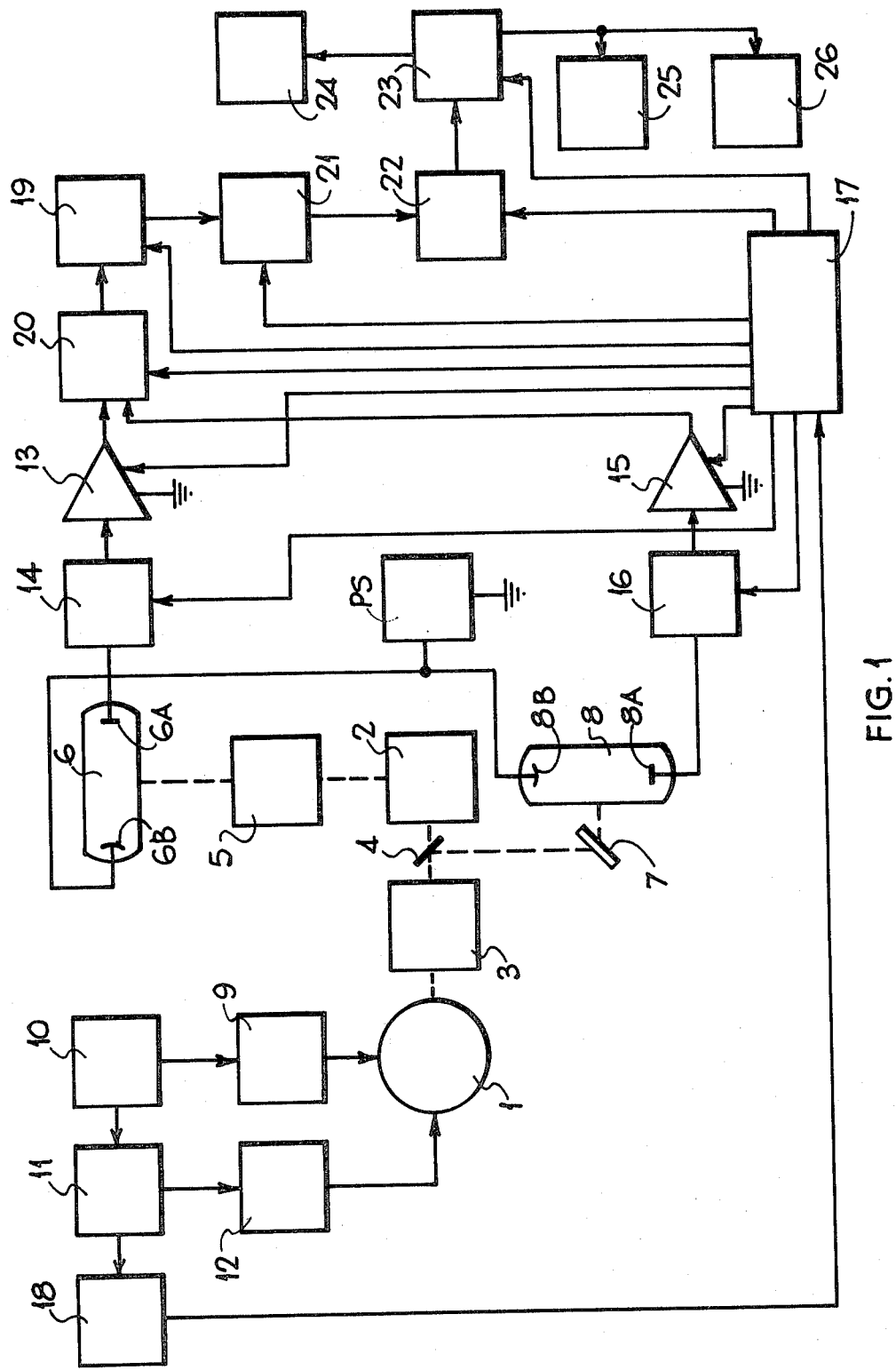
FIG. 1 is a functional diagram of a double-channel flash spectrofluorimetry layout in accordance with the present invention.

The beam splitter 4 re-directs part of the radiation from the lamp 1 onto a quantum counter 7, which, as is well known, fluoresces in proportion to the quantum efficiency of the radiation impinging thereon and is substantially irresponsive to wavelength. The fluorescence is picked up by the reference photomultiplier 8, having anode 8A and cathode 8B, and may therefore be compared with that impinging on photomultiplier 6 in terms of quantum efficiency alone, regardless of the instantaneous wavelength scanned by monochromator 3.

There is thus established the foundation of a sample fluorescence measuring channel and a reference fluorescence measuring channel which will enable the sample fluorescence measurement to be expressed as a ratio between sample fluorescence integral and reference fluorescence integral, with a view to attenuating the effect of radiation source fluctuations on said measurement.

A two-channel operation is not essential for the realization of the present invention, which is equally applicable to a spectrofluorimetric system wherein only a sample channel is used. The reason for illustrating the invention on the basis of a two-channel system is simply that such system is more complex and that the skilled in the art will have no difficulty in appreciating how it can be turned into a single channel system, essentially by the omission of certain parts, viz. units 4, 7, 8, 16 and 15, of which the last two will be introduced later.

The lamp 1 is energized in the flash mode by periodically discharging through it a capacitor of a few microfarads recharged from a high-voltage (say, 400 Volts) DC supply 9, which is derived by rectifying the output of an AC-power supply 10, normally the public supply. In FIG. 1 the capacitor is not shown but it is assumed to form part of the supply 9.

Photomultiplier 6 is connected to a DC supply PS providing a potential of approximately 1 kV between anode 6A and cathode 6B. This potential draws a standing current which, although referred to as dark current, does in fact flow whenever the photomuliplier 6 is energized, i.e. the correct potential is established between anode and cathode, whether in the dark or not.

Almost coincidently with each excitation flash produced by the lamp 1, a fluorescence flash is emitted by the sample 2, to which the photomultiplier 6 responds by generating a corresponding current pulse, superimposed on the standing current. The output of photomultiplier 6 is, therefore, a series of current pulses, each separated in time from the next by a dwell which, in relation to the peak energization power to which the lamp 1 is subjected during the capacitor discharge, is chosen so as to ensure an acceptable lamp life of, say, 500 hours. In the matter of lamp life, it has been found that if the duration of an excitation flash is contained within a few tens of microseconds, say, some 20 to 30 microseconds, and the lamp 1 is flashed at a frequency of 50–60 Hertz, enough power can be put into each flash to cause the plasma produced in the lamp by the capacitor discharge to emit a continuum of exciting radiation in the UV and near UV regions of the light spectrum adequate for spectrofluorimetric analysis without curtailing lamp life to an untolerable extent.

What has been said above with regard to the operation of photomultiplier 6 has a parallel in photomultiplier 8, which is also connected to the 1 kV supply PS. The only significant difference is that photomultiplier 8 responds to the fluorescence generated by the quantum counter 7 and not the sample 2.

In the present embodiment it will be assumed that the unit 10 represents a 210–240 Volts, 50 Hz, public supply of AC power, but naturally the apparatus could be adapted for use on a 60 Hz power supply without any difficulty. The timing of the excitation flashes is expediently arranged by causing the said capacitor to discharge through the lamp 1 when a zero-volt cross-over of chosen transition sign in the AC waveform of supply 10, say, from the positive to the negative half-wave, is sensed by zero-volt detector 11 and, as a result, a sharp firing pulse is produced by trigger pulse generator 12 which is extended to the firing electrode of the lamp 1. As in the prior art specification hereinbefore referred to, and contrary to what had been practised in earlier prior art, the transient signals are not routed straight into an integrating amplifier, because that would mean integrating the spurious contribution due to the standing current together with the desired signal quantity. Instead, the anode 6A of photomultiplier 6 is connected to an integrating amplifier 13 via an electronic switch 14. Similarly, the anode 8A of photomultiplier 8 is connected to integrating amplifier 15 via an electronic switch 16. This means, of course, that the two integrating amplifiers operate in the current integrating mode.

The electronic switches 14 and 16, which are known per se and may include FET (Field Effect Transistor) means, are controlled via a timing unit 17. They clearly must be turned on only during the occurrence of a signal. What is required for this is to determine the time relationship to the radiation source control means as well as the width of a switching pulse, in order to control its initiation and duration.

Bearing in mind that the fluorescence flash extends over a considerably longer period compared with the excitation flash and that it is desirable to ensure that substantially the whole of the fluorescence signal is collected, a 100-microsecond switching pulse is suitable. It must preferably be initiated just ahead of the excitation flash in order to ensure that substantially the whole of the signal rise and decay is included in the output signals of the photomultipliers. This is achieved in accordance with the present embodiment by deriving from the zero-volt detector 11 a signal which, just before the rise of the trigger pulse for firing the lamp 1, causes the leading edge of a square switching pulse to be generated by switching over a monostable device in unit 18 having a 100-microsecond dwell, the trailing edge of the switching pulse being generated upon the monostable device switching back to the stable state.

The 100-microsecond switching pulse is routed through the timing unit 17, which in addition to controlling the electronic switches 14 and 16 performs other functions, time related to the switching pulse.

This far the present embodiment differs only in minor respects from the embodiment described with reference to FIG. 1 in U.S. Pat. No. 4,049,970. In fact, descriptive passages relative to FIG. 1 in that specification have been incorporated in the present one with some elaboration and modification. This has been done to highlight in what follows the improvement made by the inventors upon the earlier disclosure of one of them.

The gating of the photomultipliers 6 and 8 clearly removes the effect on the photomultiplier signal due to the standing current flowing in the dwell period. In order to neutralize in addition the effect of the standing current flowing simultaneously with the signal current, the timing unit 17 incorporates a further control over the electronic switches 14 and 16 by virtue of which a further switching pulse substantially equal in duration to the switching pulse already described is introduced. The further switching pulse is made to occur during the dwell period and its timing is not critical, as will be presently shown.

There is no need to describe in detail the known technique of generating square pulses in a given time relation. It will suffice to say that the interval between the first and the second switching pulse may be arranged through a delay unit and the duration of the second switching pulse at the end of the delay through a monostable additional to monostable 18. More conveniently, the same monostable 18 may be retriggerd by the timing unit 17.

Figure 2:
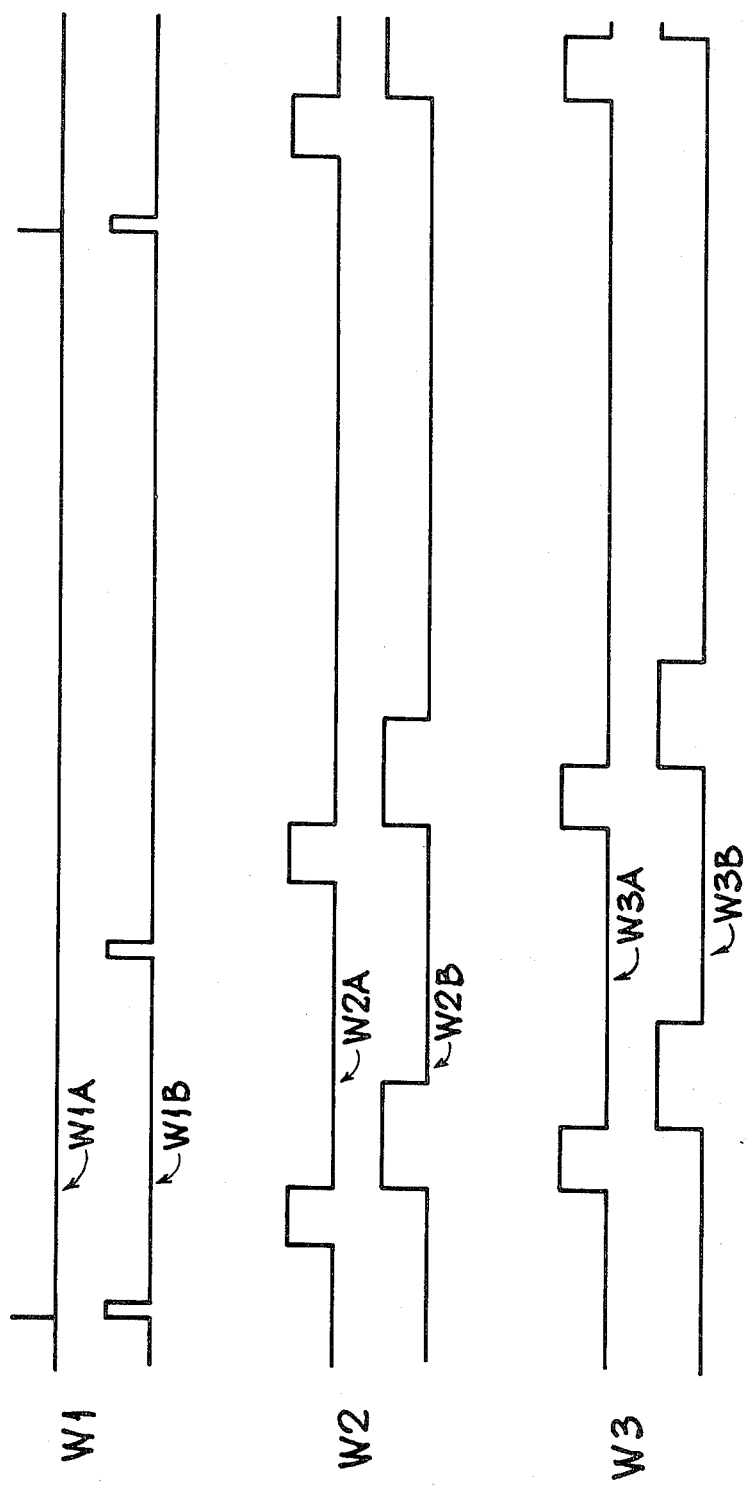
FIG. 2 is a timing diagram illustrating, in particular, the relationship between first and second integrating time interval in each channel.

The timing diagram of FIG. 2 illustrates the provision of the second switching pulse in relation to the first switching pulse and other pulses to be described later. One set of waveforms, marked W1 is common to both the sample and the reference channels; another, W2, appertains to the sample channel; and another, W3, to the reference channel. Waveform W1A depicts the firing pulse produced by the trigger pulse generator 12 at each of the zero-volt cross-overs marking the start of two successive 50 Hz AC cycles. The time lapse between the cross-overs is nominally 20 milliseconds. W1B represents the corresponding square pulses for switching on the photomultipliers during a fluorescence flash. It also represents an intermediate pulse, of the same duration as each of the other two square pulses, for switching on the photomultipliers during a small portion of the dwell period. W2A and W2B as well as W3A and W3B will be described later.

The method used for utilizing the two switching pulses so as to derive a ratio of the sample channel measurement and the reference channel measurement that is substantially free from the spurious effect caused by the dark current and other extraneous currents, i.e. the standing current, flowing both during the fluorescence signal integration period and the dwell period will now be described together with the electronic system for carrying the method into effect.

For the duration of the first switching pulse, shown as the leading pulse of waveform W1B in FIG. 2, both the sample and the reference signal will be integrated. The two integrals (each of which includes a contribution from the standing current passed during the integration period) are then converted in succession (say, sample integral followed by reference integral) from analogue to digital in a small fraction of the dwell time. The leading square pulse in waveforms W2A and W3A, respectively, marks the conversion timing.

At the end of each conversion integration is zeroed, this being indicated by the leading square pulse in waveforms W2B and W3B, respectively.

Next the second switching pulse is made to occur. This is shown as the second square pulse in waveform W1B. Integration, conversion and integration reset takes place in each channel as before, except that the quantity handled is in fact the standing current flowing through the photomultiplier during the second switching period, which as stated earlier is made identical to the first. The digitized integrals generated will be referred to as sample blank integral and reference blank integral.

The method is concluded by carrying out an arithmetical operation in which the sample blank is first subtracted from the digitized sample integral to obtain a sample difference value, the reference blank is subtracted from the digitized reference integral to obtain a reference difference value, and finally the first named difference value is divided by the second difference value to obtain a ratio expressing a fluorescence measurement of the sample which is not only substantially free from the effect of excitation source fluctuations but is also substantially free from the effect of dark current and any other extraneous current flowing during the dwell period and the fluorescence signal integration period. The two difference values and the final ratio are, of course, derived in digital form.

It is must be true that the integral of the standing current flowing during the first switching period need not be exactly equal to the integral accumulated during the second switching period but by keeping the time separation between the two periods as small as possible the difference is minimized to the point of being totally insignificant.

Turning now more particularly to the instrumental means for carrying the method into effect and referring again to FIG. 1, the analogue-to-digital conversions of the simultaneously generated fluorescence integrals in the sample and reference channels, respectively, is performed by a single analogue-to-digital converter 19, alternately connected to the output of sample integrator 13 and that of reference integrator 15 by an electronic selector switch 20. The offsetting of waveform W3A in FIG. 2 relative to waveform W2A shows that the conversion of the sample integral and the sample blank integral lead their counterparts in the reference channel. The timing of the operation is controlled by the timing unit 17, which at the end of the second conversion serving the reference channel resets both integrators and issues a coded command to arithmetic unit 21 to effect the computation referred to earlier, using the data suppled by unit 19.

The value of the ratio measurement yielded in digital form by the unit 21 is further processed in a known manner through digital filter 22, a scale expansion multiplier and offset unit 23 programmed via keyboard 24, and is finally extended to digital display 25 and digital recorder 26.

The embodiment hereinbefore described offers a number of advantages. Quite apart from the almost complete elimination of extraneous current effects, the use of the same electronic components for computing in each channel the fluorescence and the blank signals means that any offset in the components is cancelled out in the operation of subtracting the blank integral from the fluorescence integral. Furthermore, drifts in the offsets are of no consequence because the interval between the first switching period and the second switching period can be reduced to a few milliseconds out of the 20 milli-seconds intervening between successive flashes. This leads to a further advantage in that it permits the same analogue-to-digital converter to be used for both sample and reference conversions, with the result that the stability of the conversion scale factor becomes of no concern since the factor is eliminated in the computation of the fluorescence ratio.

It will be appreciated that the functions ascribed to units 23, 24 and 25 could be readily performed by computational means incorporating a microprocessor.

What is claimed is:

1. A method of flash spectrofluorimetry comprising the steps of:
   (a) subjecting a sample under analysis to a succession of high-intensity flashes of exciting radiation arranged to provide a near continuum in the spectrofluorimetric region of interest and allowing a dwell between consecutive flashes that is at least one order of magnitude greater than the duration of a single flash;
   (b) deriving through fluorescence measuring means an electrical output signal in response to the fluorescence excited in the sample by each flash, substantially the whole of said output signal occuring in a first time interval that includes a flash duration and representing a composite signal in that it includes a spurious contribution due to standing current in said fluorescence measuring means;
   (c) obtaining a first integral by integrating the composite signal during said first time interval;
   (d) disabling the spurious output of the fluorescence measuring means during the dwell period, except for a second time interval substantially equal to the first;
   (e) sampling said spurious output during the second time interval;
   (f) obtaining a second integral by integrating the sampled spurious output during said second time interval; and
   (g) subtracting the second integral from the first to obtain the integral of the true fluorescence measuring signal substantially free from said spurious contribution.

2. A method as claimed in claim 1, wherein the steps of deriving said electrical output signal and sampling the spurious output include the generation of first and second switching pulse of substantially equal duration in order to define first and second time interval, respectively, by activating the fluorescence measuring means during said intervals only.

3. A method as claimed in claim 2, wherein the steps of obtaining the first and the second integral are performed in the analogue mode on time-shared integrating means.

4. A method as claimed in claim 3, wherein the integrals are converted to digital form before the step of subtracting the second integral from the first is carried out digitally.

5. A method as claimed in claim 4, wherein the conversion is time-shared between the two integrals.

6. A method as claimed in claim 5, including the step of simultaneously applying the method to a reference channel and ratioing the sample fluorescence measuring signal with the reference measuring signal thus obtained.

7. A method as claimed in claim 6, wherein the analogue-to-digital conversion is time-shared between the two channels.

8. Apparatus for flash spectrofluorimetry, comprising:
   (a) a sample excitation arrangement including a radiation source organized to produce a succession of high-intensity excitation flashes providing a near continuum in the spectrofluorimetric region of interest, with a dwell time between two successive flashes at least one order of magnitude greater than the duration of a single flash;
   (b) fluorescence measuring means for generating an electrical output in response to the fluorescence excited in a sample under analysis by each flash emitted by said radiation source, said electrical output signal being a composite signal in that it includes an undesired contribution due to standing current in the fluorescence measuring means;
   (c) timing means in operational relationship with said excitation arrangement and the fluorescence measuring means for (I) defining a first time interval during which substantially the whole of the composite signal is made availabe, (II) disabling the output of the fluorescence measuring means during the dwell period except for a second time interval equal to the first, and (III) defining said second time interval, the first time interval including a flash duration; and
   (d) computational means in operational relationship with the fluorescence measuring means under the control of the timing means for producing the integral of the composite signal made available in the first time interval and the integral of the spurious output made available in the second time interval and for subtracting the second mentioned integral from the first whereby to obtain a true integral of the fluorescence measuring signal substantially free from said undesired contribution.

9. Apparatus as claimed in claim 8, wherein the computational means include integrating means connected to receive an input from the fluroescence measuring means for successively generating the two integrals in analogue form.

10. Apparatus as claimed in claim 9, including electronic switching means controlled by the timing means to connect the integrating means to the fluorescence measuring means for the duration of first and second time interval only.

11. Apparatus as claimed in claim 10, comprising an analogue-to-digital convertor connected to receive an input from the integrating means to convert the two integrals to digital form.

12. Apparatus as claimed in claim 11, wherein the fluorescence measuring means and the integrating means form part of a sample fluorescence measuring channel and duplicates thereof are included in a reference fluorescence measuring channel, the digital-to-analogue converter being time-shared by the two channels via a selector controlled by the timing means.

13. Apparatus as claimed in claim 12, wherein the computational means include an arithmetic unit for performing digital subtraction of said second mentioned integral from the said first mentioned integral after their conversion to digital form in both the sample and the reference channel and for ratioing the resulting sample fluorescence measuring signal with the resulting reference fluorescence measuring signal.

14. Apparatus as claimed in claim 8, wherein the radiation source is a plasma discharge source and the fluorescence measuring means is a photomultiplier.

15. Apparatus as claimed in claim 8, wherein the apparatus is powered from an AC public supply and the timing means include a zero-volt detector of the AC waveform to relate all timing operations to a cross-over point of chosen sign transition in said waveform.

* * * * *